(12) United States Patent
Han (10) Patent No.: US 8,721,574 B2
(45) Date of Patent: May 13, 2014

(54) SKIN STIMULATOR

(75) Inventor: Ki-soo Han, Seoul (KR)

(73) Assignee: DTS Lab Co., Ltd, Seoul (KR)

( * ) Notice: Subject to any disclaimer, the term of this patent is extended or adjusted under 35 U.S.C. 154(b) by 581 days.

(21) Appl. No.: 13/055,735

(22) PCT Filed: Sep. 2, 2009

(86) PCT No.: PCT/KR2009/004936
§ 371 (c)(1),
(2), (4) Date: Jan. 25, 2011

(87) PCT Pub. No.: WO2010/027188
PCT Pub. Date: Mar. 11, 2010

(65) Prior Publication Data
US 2011/0172574 A1    Jul. 14, 2011

(30) Foreign Application Priority Data

| Sep. 3, 2008 | (KR) | 10-2008-0086758 |
| Sep. 23, 2008 | (KR) | 10-2008-0092995 |
| Dec. 1, 2008 | (KR) | 10-2008-0120473 |
| Dec. 1, 2008 | (KR) | 10-2008-0120474 |
| Dec. 2, 2008 | (KR) | 10-2008-0120971 |

(51) Int. Cl.
*A61H 15/00* (2006.01)

(52) U.S. Cl.
USPC .......................... 601/119; 601/120; 601/125

(58) Field of Classification Search
CPC ................. A61H 15/0092; A61H 2015/0035; A61H 2015/0014; A61H 2201/1695; A61H 2201/1685; A61M 37/0015
USPC ......... 601/112, 114, 118, 119, 120, 121, 122, 601/123, 125, 128, 134
See application file for complete search history.

(56) References Cited

U.S. PATENT DOCUMENTS

| 4,993,408 A * | 2/1991 | Schweisfurth | 601/123 |
| 2003/0100936 A1 | 5/2003 | Altshuler et al. | |
| 2007/0288078 A1* | 12/2007 | Livneh | 607/147 |
| 2008/0161735 A1* | 7/2008 | Lee et al. | 601/125 |
| 2008/0294116 A1* | 11/2008 | Wolter et al. | 604/173 |
| 2009/0312691 A1* | 12/2009 | Kim et al. | 604/22 |
| 2013/0150878 A1* | 6/2013 | Church | 606/189 |

FOREIGN PATENT DOCUMENTS

| EP | 0619996 | 10/1994 |
| KR | 20-0238622 | 10/2001 |
| KR | 20-2008-0003473 | 8/2008 |

* cited by examiner

*Primary Examiner* — Quang D Thanh
(74) *Attorney, Agent, or Firm* — Lexyoume IP Meister, PLLC (57) ABSTRACT

A skin stimulator which can be produced through a simple process in which a circular disc of a drum is formed by integrating a metal disc having needles on a circumferential surface thereof with a reinforcing resin material using insert injection molding and layering a plurality of metal discs and retainers, thus increasing productivity and economic efficiency, realizing stable operation and preventing foreign substances from being jammed in the drum, and which is configured such that, when pricking the skin with the needles, the needles do not give severe damage to the skin and can be prevented from being broken, thus being effectively used for a lengthy period of time, and in which each of the needles forms a polygonal cross-section of at least six sides instead of a circular cross section, so that, when pricking the skin with the needles, the contact surface of each needle relative to the skin can be reduced, thus minimizing the pain.

4 Claims, 7 Drawing Sheets

SKIN STIMULATOR

TECHNICAL FIELD

The present invention relates, in general, to skin stimulators and, more particularly, to a skin stimulator configured such that a plurality of circular discs having needles on a circumferential surface thereof and a retainer spacing the circular discs apart from each other have respective simple structures and are closely assembled with each other, and form a drum in which the discs and the retainer can be prevented from being undesirably moved relative to each other, so that dirt dropped from the skin are not jammed in the drum and, when pricking the skin with the needles, the needles do not give severe damage to the skin and can be prevented from being broken, thus being effectively used for a lengthy period of time.

Further, each of the needles used in the present invention is configured to form a polygonal cross-section of at least six sides instead of a circular cross section, so that, when pricking the skin with the needles, the contact surface of each needle relative to the skin can be reduced, thus minimizing the pain.

BACKGROUND ART

The symptoms of senility of the skin, that is, the wrinkles formed on the skin generally relate to collagen in the dermis, which is the layer below the epidermis.

The dermis has about 0.7 mm to 4 mm thickness and is several times thicker than the epidermis. The senility of the skin is caused by the fact that the amount of collagen in the dermis is gradually reduced, thus drying the skin and forming wrinkles on the skin.

To retard the senility of the skin or to remove the wrinkles from the skin, it is required to continuously fill up a deficiency of collagen or to supply new collagen to the skin. In the related art, to accomplish the object, nutritive elements, such as Vitamin C or peptide required to produce collagen, are applied or sprayed onto the skin.

However, the above-mentioned method in which the nutritive elements, such as Vitamin C or peptide, are applied or sprayed onto the skin is problematic in that 99.7% of the applied or sprayed nutritive elements cannot pass through the stratum corneum, which is the outermost layer of the skin, but remain on the skin and finally disappear, and only 0.3% of the applied or sprayed nutritive elements can infiltrate into the dermis, so that the method is inefficient.

In an effort to overcome the problems, a skin stimulator (so-called "microneedle") has been proposed and used. The skin stimulator is provided with sharp needles, which stimulate the skin and form a microchannel in the skin, thus supplying nutritive elements, such as Vitamin or peptide required to produce collagen, to the dermis of the skin and making the collagen be efficiently produced in the dermis.

An example of the skin stimulators may be referred to Korean Utility Model Registration No. 20-395359 (entitled a microneedle roller). As disclosed in the official gazette (Publication of Correction), the microneedle roller comprises a roller, which is formed by layering at least one circular disc, and at least one microneedle, which is formed in the circular disc or on a surface of the circular disc such that the microneedle can be exposed outside the outer surface of the roller.

The production or supplement of collagen in the dermis by stimulating the skin using the microneedles (sharp needles) of the roller can be realized with the following theory.

That is, when the skin is compressed using sharp needles, a microchannel can be formed in the skin tissue.

In the above state, when the skin tissue gets a microwound by the microneedles, new tissue can be formed in the microwound due to the natural healing force of the skin, so that the wounded skin tissue can revive as resilient new tissue.

Further, the revival of the resilient new skin tissue must be accompanied by the recovery of collagen in the dermis due to the natural healing force curing the wounded skin, thus realizing the production and supplement of collagen.

However, the above-mentioned conventional skin stimulator is problematic as follows due to the structure thereof.

In the skin stimulator, the needles must be securely inserted into respective holes formed in the circular disc one by one, so that the productivity of the skin stimulator is reduced, thereby increasing the production cost and reducing economic efficiency of the skin stimulator.

Further, it is almost impossible to securely or closely assemble the circular discs with each other such that the discs are not undesirably moved, so that the conventional skin stimulator cannot effectively stimulate the skin and the needles may be broken at the tips thereof. Further, the broken tips of the needles may cause severe injuries in the skin tissue.

Further, the needles used in the conventional skin stimulator are thin, long needles having a circular cross-section, so that, when pricking the skin with the needles, the needles pass through pain spots in the body, thus making a user feel a pain.

DISCLOSURE

Technical Problem

The present invention has been made to solve the above problems occurring in the related art.

Accordingly, the present invention is intended to provide a skin stimulator, which can be produced through a simple process in which a circular disc of a drum is formed by integrating a metal disc having a plurality of needles on a circumferential surface thereof with a reinforcing resin material using insert injection molding and layering a plurality of metal discs and retainers, thus increasing productivity and economic efficiency, and which is configured such that, when pricking the skin with the needles, the needles do not give severe damage to the skin and can be prevented from being broken, thus being effectively used for a lengthy period of time.

Further, the present invention serves to provide a skin stimulator, in which each of the needles provided on the circumferential surface of the drum is configured to form a polygonal cross-section of at least six sides instead of a circular cross section, so that, when pricking the skin with the needles, the contact surface of each needle relative to the skin can be reduced, thus minimizing the pain.

The present invention also serves to provide a skin stimulator, in which the circular discs and the retainers of the drum have respective simple structures and are closely assembled with each other such that the discs and the retainers can be prevented from being undesirably moved relative to each other, thus realizing stable operation of the skin stimulator and preventing foreign substances from being jammed in the drum.

Technical Solution

In an aspect, the present invention provides a skin stimulator, comprising:

a drum comprising a circular disc having a plurality of needles on a circumferential surface thereof, and a retainer spacing a plurality of circular discs apart from each other; and a handle to which a drum shaft is held so that the drum shaft can be rolled, wherein the circular disc comprises a metal disc having the needles on a circumferential surface thereof and a plurality of locking holes formed therethrough, and is formed by integrating the metal disc with a reinforcing resin material using insert injection molding or heat fusion in which the surface of the metal disc is covered with the reinforcing resin material such that the needles are exposed outside the reinforcing resin material, the reinforcing resin material having a shaft hole at a center thereof so as to receive the drum shaft, and the retainer is provided with a depression formed in each side surface thereof and having a depth to receive thickness of the reinforcing resin material covering the surface of the metal disc, with a plurality of micro protrusions formed on an edge rim of the depression such that the micro protrusions are spaced apart from each other at regular intervals.

In the present invention, each of the needles regularly arranged on the circumferential surface of the circular disc of the drum may be provided with inclined surfaces on corners of opposite surfaces thereof such that the inclined surfaces form a tip of each of the needles into a polygonal shape of at least six sides. Therefore, when pricking the skin with the needles, the contact surface of each needle relative to the skin can be reduced, thus minimizing the pain.

In the present invention, the circular disc of the drum may be provided with a plurality of locking holes or a plurality of locking grooves formed therethrough, and the retainer may be provided with a plurality of protrusions formed on each side surface thereof and inserted into the locking holes or the locking grooves. Therefore, the circular discs and the retainers can be closely assembled with each other such that they can be operated without being moved relative to each other, thus realizing stable operation of the skin stimulator and preventing foreign substances from being jammed in the drum.

DESCRIPTION OF REFERENCE CHARACTERS OF IMPORTANT PARTS

| 1: | skin stimulator | 2: | needles |
|---|---|---|---|
| 3: | drum | 4: | drum shaft |
| 5: | circular disc | 6: | locking hole |
| 7: | metal disc | 8: | reinforcing resin material |
| 13: | end plate | 18: | reinforcing resin material |
| 19, 119: | retainer | 20: | depression |
| 21: | edge rim | 22: | micro protrusions |
| 100: | inclined surface | 200: | protrusions |

BEST MODE

Hereinbelow, a skin stimulator according to a preferred embodiment of the present invention will be described in detail with reference to the accompanying drawings.

As shown in FIG. 1 through FIG. 5, a skin stimulator 1 according to an embodiment of the present invention stimulates the skin and comprises a drum 3 having a plurality of needles 2 on an outer surface thereof, and a handle H rotatably held to a drum shaft 4 of the drum 3 such that the drum shaft can be rolled. The drum 3 comprises a plurality of circular discs 5 rotatably held on the drum shaft 4. Each of the circular discs 5 comprises a metal disc 7 having the needles 2 on a circumferential surface thereof and a plurality of locking holes 6 formed therethrough, and is formed by integrating the metal disc 7 with a reinforcing resin material 8 using insert injection molding in which the surface of the metal disc 7 is covered with the reinforcing resin material 8 such that the needles 2 are exposed outside the reinforcing resin material. The reinforcing resin material 8 has a shaft hole 9 at a center thereof so as to receive the drum shaft 4.

In other words, the metal disc 7 and the reinforcing resin material 8 made of different materials are integrated with each other using insert injection molding such that the needles 2 can be stably retained in respective locations without being removed or separated from the reinforcing rein material 8.

Further, in the molding process, the reinforcing resin material 8 fills the locking holes 6 formed through the metal disc 7, thus realizing strong integration of the reinforcing resin material with the metal disc.

It is preferred that the circular discs 5 be closely assembled with each other by physical pressure. However, the circular discs 5 may be integrated with each other by welding the reinforcing resin materials 8 of the discs 5 to each other using ultrasonic welding.

In another embodiment shown in FIG. 6 through FIG. 9, the present invention provides a skin stimulator, which stimulates the skin and comprises a drum 3 having a plurality of needles 2 on an outer surface thereof, and a handle H rotatably held to a drum shaft 4 of the drum 3 such that the drum shaft can be rolled. The drum 3 comprises a plurality of circular discs 5 rotatably held on the drum shaft 4. Each of the circular discs 5 comprises a metal disc 7 having the needles 2 on a circumferential surface thereof and a plurality of locking holes 6 formed therethrough, and is formed by integrating the metal disc 7 with a reinforcing resin material 18 using insert injection molding or heat fusion in which the surface of the metal disc 7 is covered with the reinforcing resin material 18 such that the needles 2 are exposed outside the reinforcing resin material. The reinforcing resin material 18 has a shaft hole 9 at a center thereof so as to receive the drum shaft 4.

Further, a retainer 19 is used for spacing the circular discs apart from each other. The retainer 19 is provided with a depression 20, which is formed in each side surface of the retainer and has a depth to receive thickness of the reinforcing resin material covering the surface of the metal disc, with a plurality of micro protrusions 22 formed on an edge rim 21 of the depression 20 such that the micro protrusions are spaced apart from each other at regular intervals.

Here, the number of the micro protrusions 22 is preferably set to three to eight. However, the inner surface of the edge rim may be configured to be entirely rugged.

The reference numeral 13 denotes an end plate.

Hereinbelow, the operation of the present invention will be described.

Figure 1:
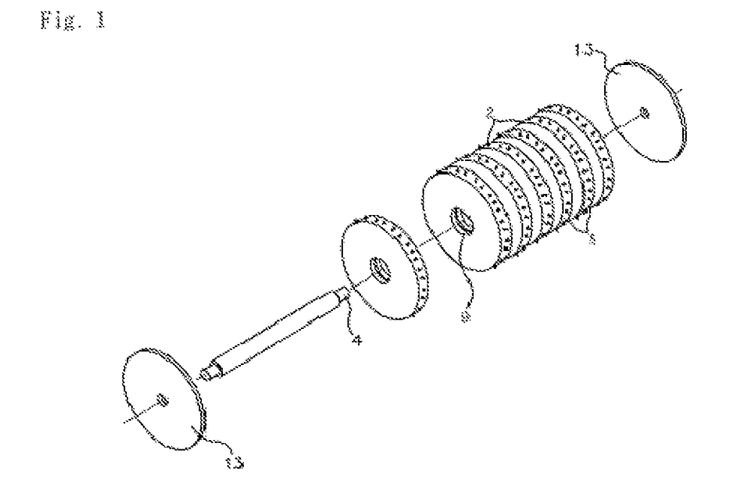
FIG. 1 is a perspective view of a skin stimulator according to an embodiment of the present invention in a partially exploded state.
Figure 2:
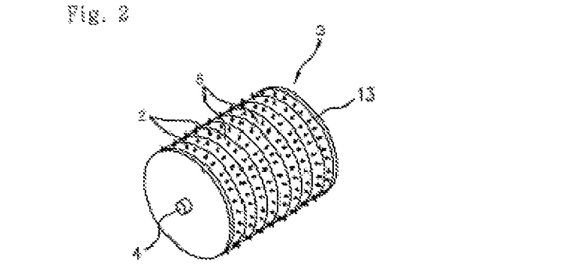
FIG. 2 is a perspective view of the skin stimulator of FIG. 1 in an assembled state.
Figure 3:
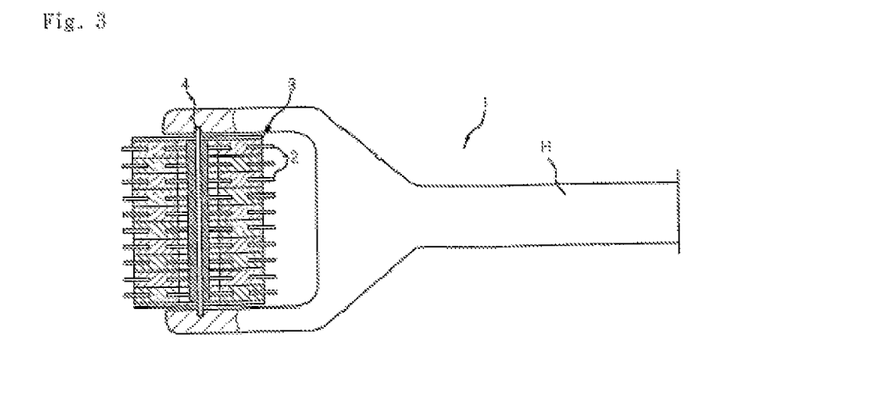
FIG. 3 is a partially sectioned view of FIG. 2.
Figure 4:
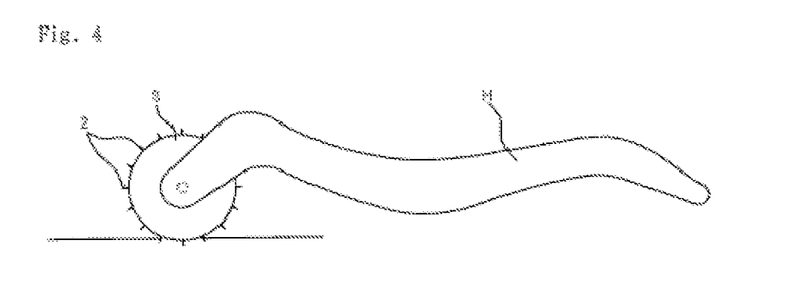
FIG. 4 is a view illustrating the operation of the present invention.
Figure 5:
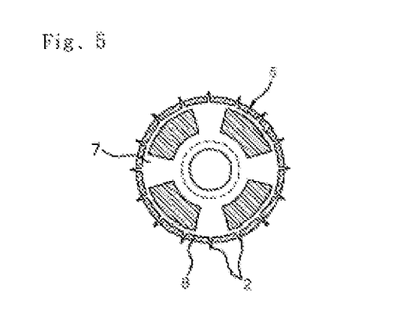
FIG. 5 is a partially sectioned view of FIG. 2.
Figure 6:
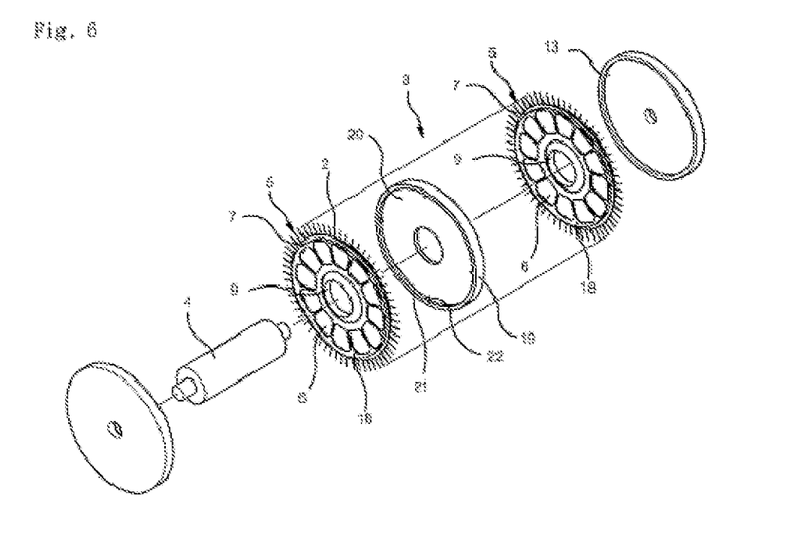
FIG. 6 is a perspective view of a skin stimulator according to another embodiment of the present invention in a partially exploded state.
Figure 7:
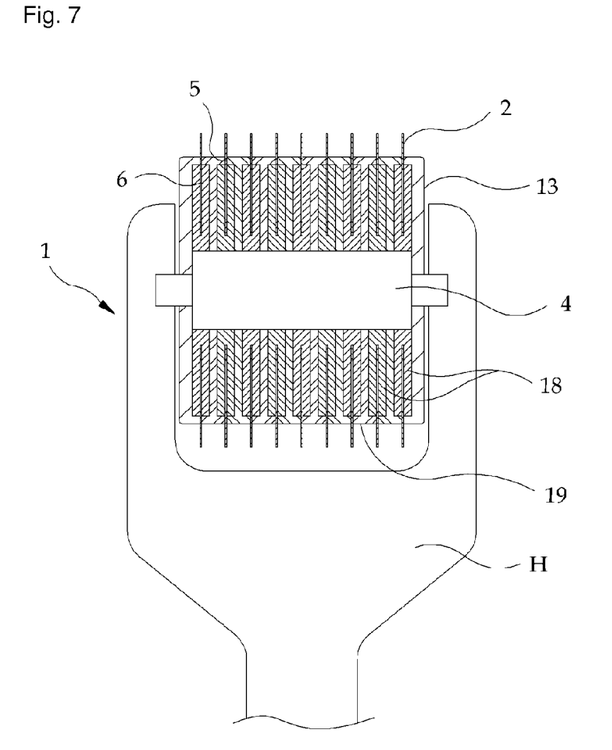
FIG. 7 is a sectional view of FIG. 6.
Figure 8:
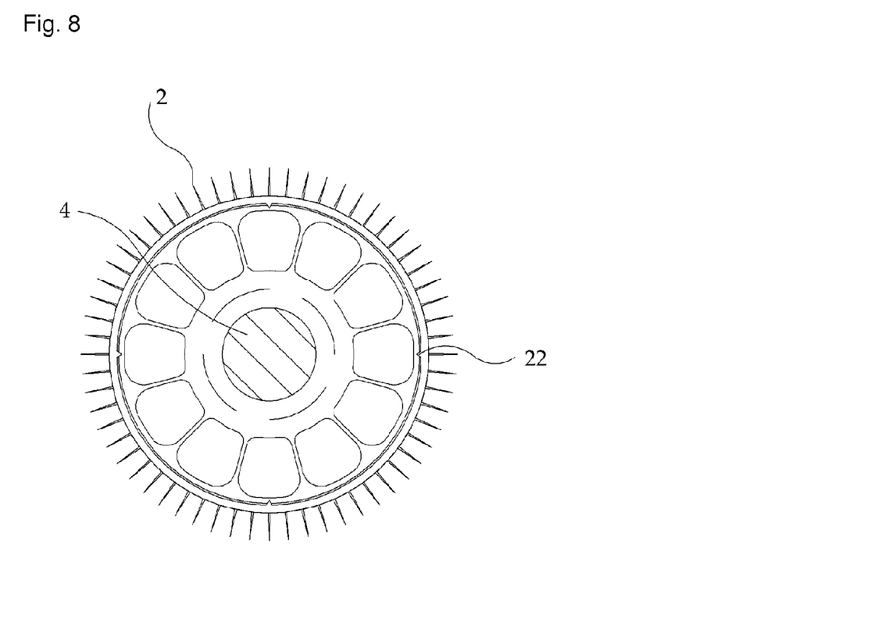
FIG. 8 is a sectional view illustrating a circular disc of FIG. 6.
Figure 9:
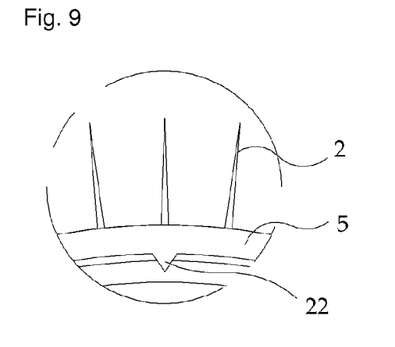
FIG. 9 is a partially enlarged view of FIG. 8.

A user grips the handle H with a hand and rolls the drum 3 on the skin, thus compressing the skin.

That is, when the drum 3 is rolled on the skin, the needles 2 of the drum stimulate the skin.

In the above state, the rolling drum 3 can effectively move on the skin and can effectively stimulate the skin.

Further, the circular discs 5 and the retainers 19 in the drum are closely fixed to each other without being moved relative to each other, so that the needles can effectively stimulate the skin and, when pricking the skin with the needles, the needles do not give severe damage to the skin and can be prevented from being broken, thus being effectively used for a lengthy period of time. Further, dirt dropped from the skin can be prevented from being jammed in the drum, so that the skin stimulator can be used clean.

In the skin stimulated by the skin stimulator 1 according to the present invention, production and supplement of collagen can be effectively realized, thus promoting the health of the skin.

Figure 10:
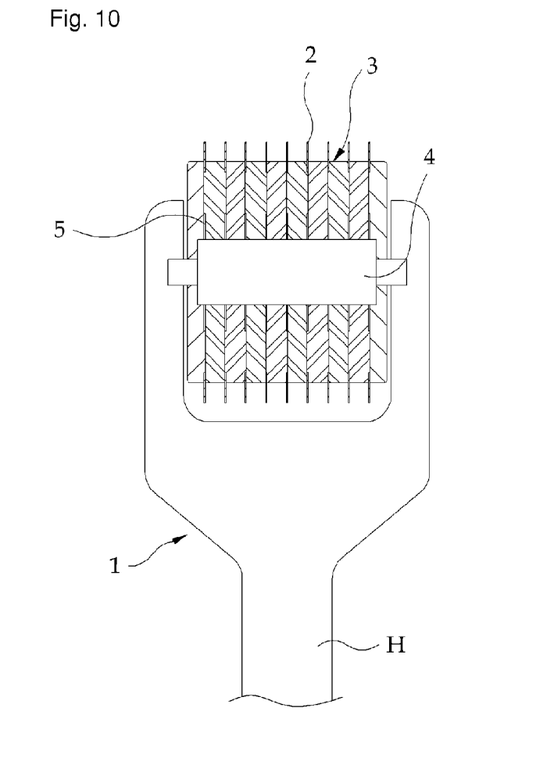
FIG. 10 is a partially sectioned view of a further embodiment of the present invention.
Figure 11:
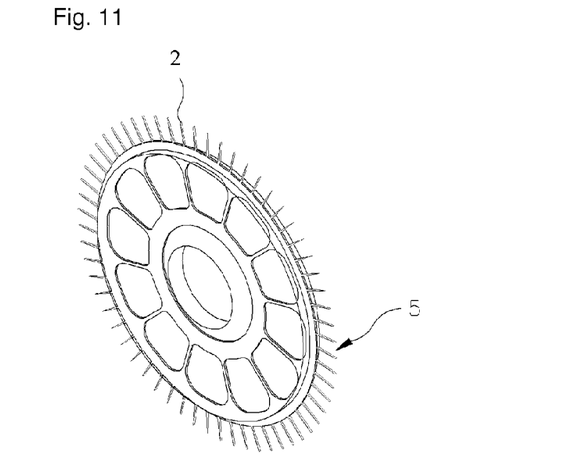
FIG. 11 is a perspective view illustrating a circular disc of FIG. 10.
Figure 12:
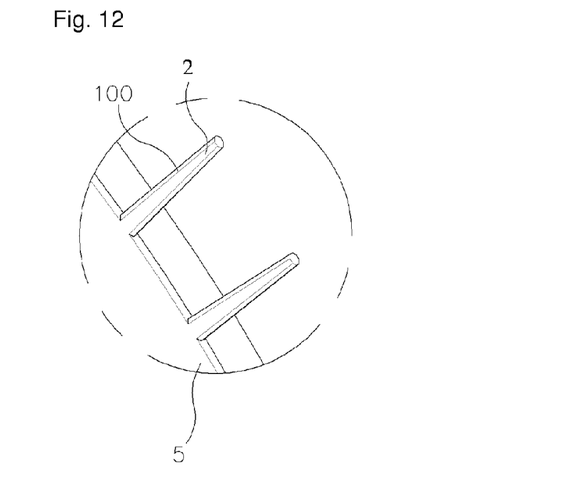
FIG. 12 is a partially enlarged perspective view of FIG. 11.

Further, the skin stimulator 1 according to the present invention may be altered as shown in FIG. 10 through FIG. 12. Here, the skin stimulator comprises: a drum 3 comprising a circular disc 5 having a plurality of needles 2 on a circumferential surface thereof, and a retainer spacing a plurality of circular discs apart from each other; and a handle H to which a drum shaft 4 is held so that the drum shaft can be rolled, wherein each of the needles 2 regularly arranged on the circumferential surface of the circular disc 5 is provided with inclined surfaces 100 on corners of opposite surfaces such that the inclined surfaces 100 form a tip of each of the needles 2 into a polygonal shape of at least six sides.

The skin stimulator according to the second embodiment of the present invention will be operated in the same manner as that described for the first embodiment, but, when pricking the skin with the tips of the needles 2, the restoring force of the skin is influenced by the polygonal shape of at least six sides in the tip of each needle 2, so that the contact surface of each needle relative to the pain spots in the skin can be reduced, thus minimizing the pain.

Figure 13:
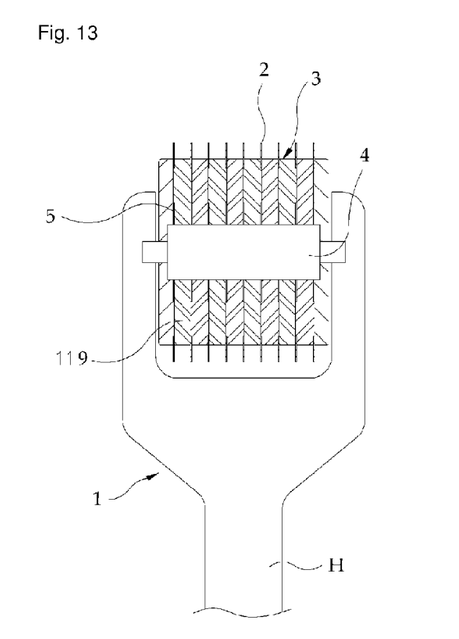
FIG. 13 is a partially sectioned view of yet another embodiment of the present invention.
Figure 14:
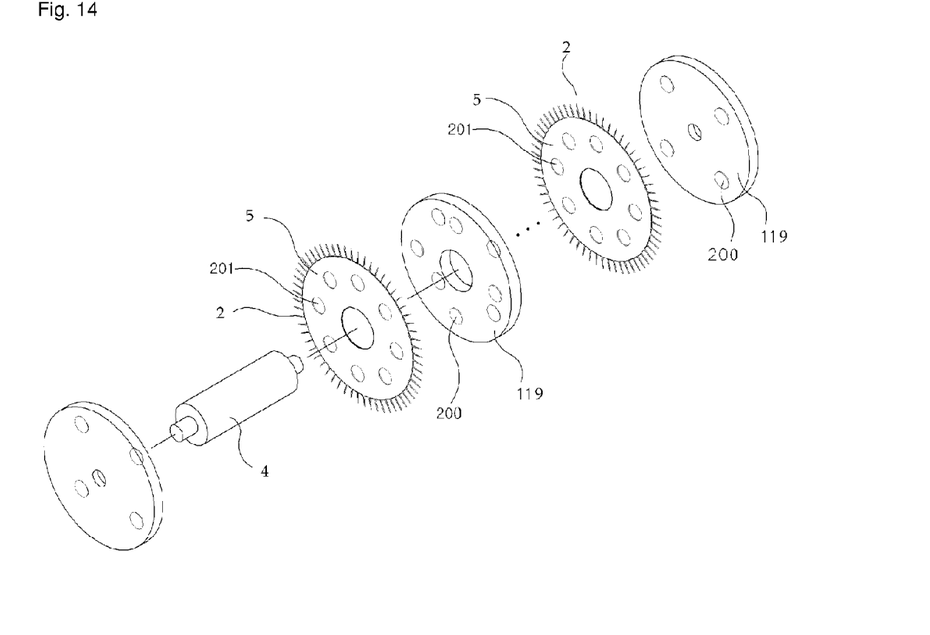
FIG. 14 is an exploded perspective view of FIG. 13.
Figure 15:
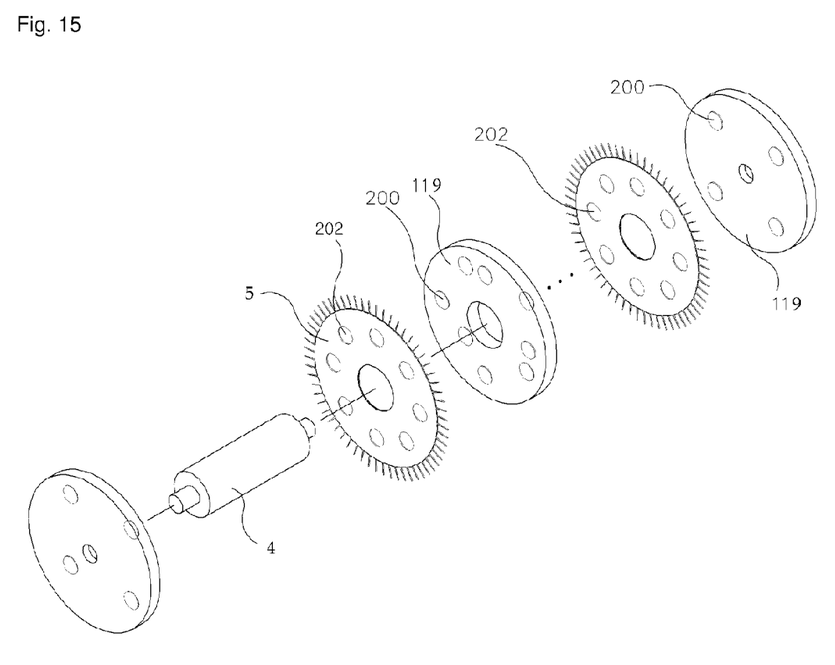
FIG. 15 is an exploded perspective view illustrating another embodiment of FIG. 13.

The skin stimulator 1 according to the present invention may be further altered as shown in FIG. 13 through FIG. 15. Here, the skin stimulator comprises: a drum 3 comprising a circular disc 5 having a plurality of needles 2 on a circumferential surface thereof, and a retainer 119 spacing a plurality of circular discs apart from each other; and a handle H to which a drum shaft 4 is held so that the drum shaft can be rolled, wherein the circular disc 5 of the drum 3 is provided with a plurality of locking holes 201 or a plurality of locking grooves 202 formed therethrough, and the retainer 119 is provided with a plurality of protrusions 200 formed on each side surface thereof and inserted into the locking holes or the locking grooves.

Here, the protruding length of the protrusions 200 may be set to be equal to the depth of respective locking grooves in the case of the locking grooves formed in the circular disc or may be equal to thickness of the circular disc 5 in the case of the locking holes formed in the circular disc.

To use the skin stimulator according to the third embodiment, a user grips the handle H with a hand and rolls the drum 3 on the skin, thus compressing the skin and stimulating the skin by the needles 2.

In the above state, the skin stimulator is operated in a state in which the protrusions 200 of the retainer 119 are fixed to the locking holes 201 or the locking grooves 202 of the circular disc 5 such that the circular disc and the retainer are not spaced apart from each other. Thus, when pricking the skin with the needles 2, dirt dropped from the skin or other foreign substances can be prevented from being jammed between the circular disc 5 and the retainer 9, so that, unlike the conventional skin stimulator, the skin stimulator of the present invention can be kept clean.

INDUSTRIAL APPLICABILITY

The skin stimulator of the present invention can be produced through a simple process in which a circular disc of a drum is formed by integrating a metal disc having a plurality of needles on a circumferential surface thereof with a reinforcing resin material using insert injection molding and closely layering a plurality of metal discs and retainers such that the metal discs and the retainers are not moved relative too each other, thus increasing productivity and economic efficiency. The present invention also realizes stable operation of the skin stimulator and prevents foreign substances from being jammed in the drum, thus preventing propagation of bacteria in the drum. Further, when pricking the skin with the needles, the needles do not give severe damage to the skin and can be prevented from being broken, thus being effectively used for a lengthy period of time.

Further, each of the needles provided on the circumferential surface of the drum is configured to form a polygonal cross-section of at least six sides instead of a circular cross section, so that, when pricking the skin with the needles, the contact surface of each needle relative to the skin can be reduced, thus minimizing the pain.

The invention claimed is:

1. A skin stimulator, comprising: a drum comprising a circular disc having a plurality of needles on a circumferential surface thereof, and a retainer spacing a plurality of circular discs apart from each other; and a handle to which a drum shaft is held so that the drum shaft can be rolled, wherein the circular disc comprises a metal disc having the needles on a circumferential surface thereof and a plurality of locking holes formed therethrough, and is formed by integrating the metal disc with a reinforcing resin material using insert injection molding or heat fusion in which the surface of the metal disc is covered with the reinforcing resin material such that the needles are exposed outside the reinforcing resin material, the reinforcing resin material having a shaft hole at a center thereof so as to receive the drum shaft, and the retainer is provided with a depression formed in each side surface thereof and having a depth to receive thickness of the reinforcing resin material covering the surface of the metal disc, with a plurality of micro protrusions formed on an edge rim of the depression such that the micro protrusions are spaced apart from each other at regular intervals.

2. The skin stimulator according to claim 1, wherein each of the micro protrusions gradually tapers to a point in a direction of an inner end thereof.

3. The skin stimulator according to claim 1, wherein the micro protrusions comprise three to eight protrusions formed on the edge rim at regular intervals.

4. A skin stimulator, comprising: a drum comprising a circular disc having a plurality of needles on a circumferential surface thereof and a retainer spacing a plurality of circular discs apart from each other; and a handle to which a drum shaft is held so that the drum shaft can be rolled, wherein the circular disc of the drum is provided with a plurality of locking holes or a plurality of locking grooves formed therethrough, and the retainer is provided with a plurality of protrusions formed on each side surface thereof and inserted into the locking holes or the locking grooves.

* * * * *